(12) United States Patent
Saito

(10) Patent No.: US 10,195,133 B2
(45) Date of Patent: Feb. 5, 2019

(54) PHOTOCURABLE COMPOSITION FOR NAIL OR ARTIFICIAL NAIL

(71) Applicant: THREE BOND CO., LTD., Hachioji-shi, Tokyo (JP)

(72) Inventor: Erika Saito, Hachioji (JP)

(73) Assignee: THREE BOND CO., LTD., Hachioji-Shi, Tokyo ( * ) Notice: Subject to any disclaimer, the term of this patent is extended or adjusted under 35 U.S.C. 154(b) by 0 days.

(21) Appl. No.: 15/366,363

(22) Filed: Dec. 1, 2016

(65) Prior Publication Data
US 2017/0157022 A1 Jun. 8, 2017

(30) Foreign Application Priority Data

Dec. 2, 2015 (JP) ................................ 2015-235286

(51) Int. Cl.
| | | |
|---|---|---|
| *A61K 8/81* | (2006.01) | |
| *A61Q 3/02* | (2006.01) | |
| *A61K 8/35* | (2006.01) | |
| *A61K 8/55* | (2006.01) | |
| *A45D 29/00* | (2006.01) | |

(52) U.S. Cl.
CPC ............ *A61K 8/8147* (2013.01); *A45D 29/00* (2013.01); *A61K 8/35* (2013.01); *A61K 8/55* (2013.01); *A61Q 3/02* (2013.01); *A61K 2800/81* (2013.01)

(58) Field of Classification Search
None
See application file for complete search history.

(56) References Cited

U.S. PATENT DOCUMENTS

| | | | |
|---|---|---|---|
| 6,391,938 B1* | 5/2002 | Lilley ................. | A61K 8/8152 252/182.13 |
| 2014/0261512 A1* | 9/2014 | Nordstrom ............... | A61Q 3/02 132/200 |
| 2016/0250136 A1* | 9/2016 | Bryson ................ | A61K 8/4973 424/401 |

FOREIGN PATENT DOCUMENTS

WO     WO 2012/140796 A1     10/2012

OTHER PUBLICATIONS

PubChem. National Center for Biotechnology Information. PubChem Compound Database; CID=18689, <https://pubchem.ncbi.nlm.nih.gov/compound/18689> (accessed Jun. 7, 2018) (Year: 2018).*

* cited by examiner

*Primary Examiner* — Nicole P Babson
(74) *Attorney, Agent, or Firm* — Dickinson Wright PLLC

(57) ABSTRACT

The present invention relates to a photocurable composition for coating a nail or an artificial nail, including:
a component (A): an acrylate oligomer;
a component (B): a methacrylate monomer; and
a component (C): a photopolymerization initiator.
The present invention provides a photocurable composition for coating a nail or an artificial nail, which has a small amount of heat generation during curing by light irradiation.

10 Claims, 5 Drawing Sheets

[FIG. 1A]
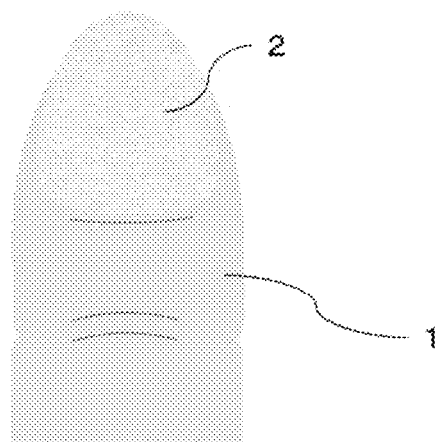
[FIG. 1B]
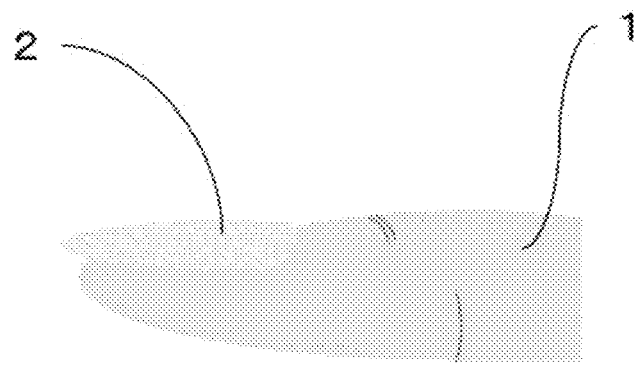

[FIG. 2]
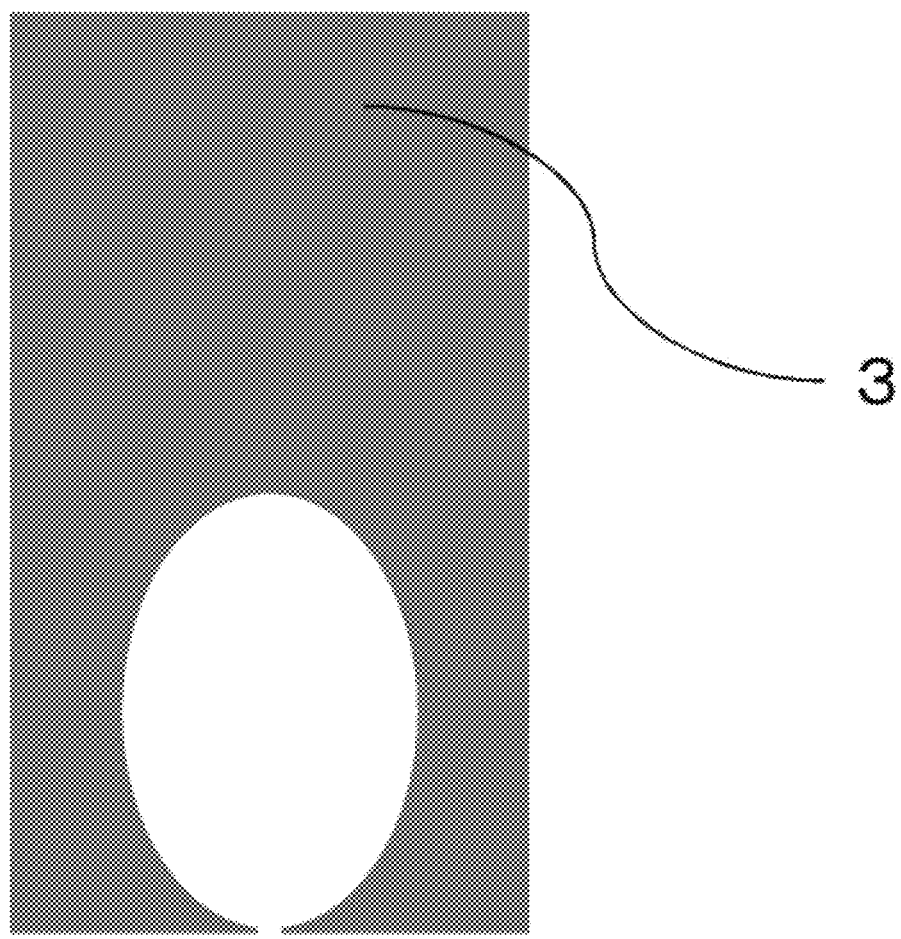

[FIG. 3A]
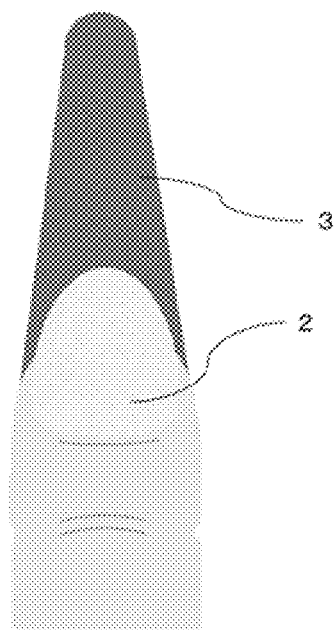
[FIG. 3B]
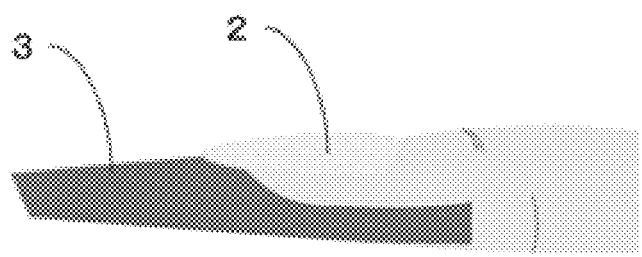

[FIG. 4]
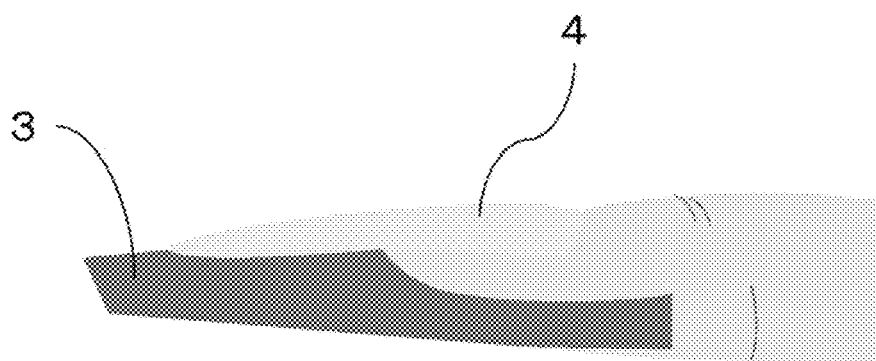
[FIG. 5]
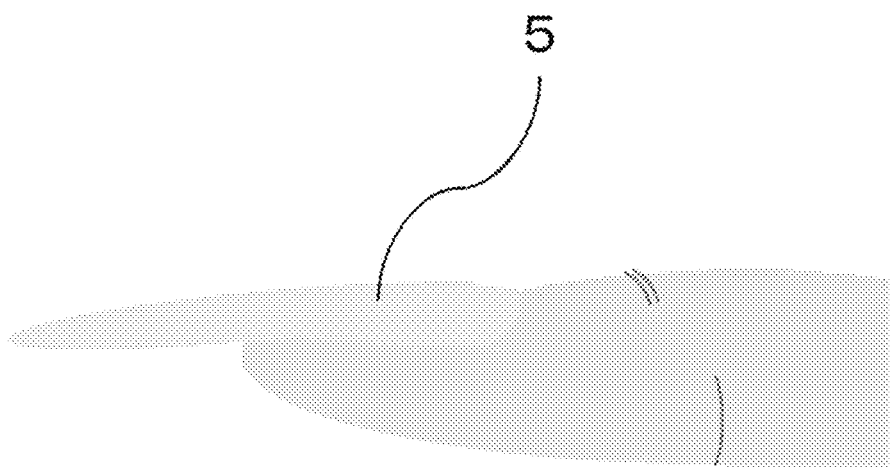

[FIG. 6]
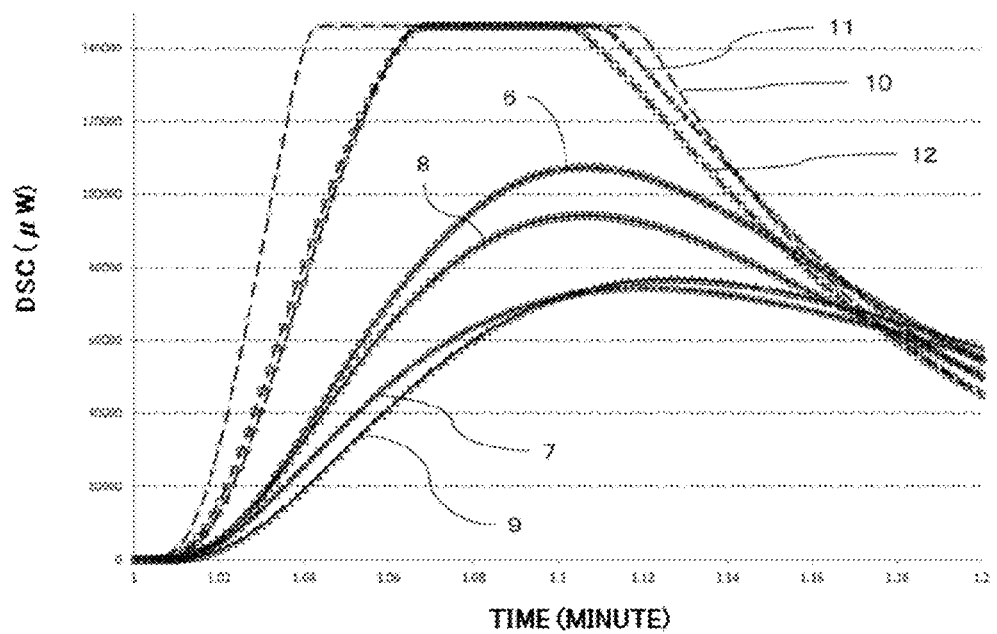

PHOTOCURABLE COMPOSITION FOR NAIL OR ARTIFICIAL NAIL

CROSS-REFERENCE TO RELATED APPLICATION

This application is based on Japanese Patent Application No. 2015-235286 filed on Dec. 2, 2015, the contents of which are incorporated herein by reference.

BACKGROUND

1. Technical Field

The present invention relates to a photocurable composition for coating a nail or an artificial nail.

Particularly, the present invention relates to a photocurable composition for coating a nail or an artificial nail, suitably used for a sculptured nail.

2. Description of Related Arts

In a field of a nail decoration, a photocurable composition for coating a nail or an artificial nail (UV nail gel) is used. Specifically, a UV nail gel used for a sculptured nail is known. When a sculptured nail is formed, a process for interposing a seal mount called a form between a nail (natural nail) and a fingertip, applying a UV nail gel on the nail and the form, and then photocuring the gel is repeated to coat (decorate) the nail. By such a method, the nail can be decorated such that the nail gel is integrated with the nail without bonding a nail chip or the like to the nail. Therefore, decoration having excellent durability can be performed while the nail chip or the like is hardly peeled off.

As an invention relating to such decoration of a nail, WO 2012/140796 A discloses a method for bonding a nonwoven fabric as a flexible substrate having a liquid-absorbing property to a nail and then impregnating the nonwoven fabric with a UV nail gel.

SUMMARY

However, when a nonwoven fabric is used, transparency of a nail after decoration cannot be exhibited, a shape is not easily maintained with the nonwoven fabric, and a distortion or the like occurs in a decorated portion of the nail. Backgrounds for generating the method of the invention disclosed in WO 2012/140796 A are as follows. That is, when a UV nail gel used has low curability, curability in a deep portion thereof is lowered, and it takes long time before curing is terminated. On the other hand, when the gel has high curability, the gel generates heat during curing by UV irradiation or the like, and therefore a burden on a finger is increased disadvantageously. Particularly, there is a problem that such a burden by heat generation is not preferable because application of a large amount of UV nail gel on a nail increases the amount of heat generation.

As described above, conventionally, it has been difficult to realize a photocurable composition for coating a nail or an artificial nail suitable for a sculptured nail, which has a small amount of heat generation during curing by light irradiation. Therefore, an object of the present invention is to provide a photocurable composition for coating a nail or an artificial nail, which has a small amount of heat generation during curing by light irradiation.

The present inventors made intensive studies. As a result, the present inventors have found that the above object can be achieved by a photocurable composition for coating a nail or an artificial nail having the following configuration, and have completed the present invention.

An embodiment of the present invention is a photocurable composition for coating a nail or an artificial nail, containing:
 a component (A): an acrylate oligomer;
 a component (B): a methacrylate monomer; and
 a component (C): a photopolymerization initiator.

BRIEF DESCRIPTION OF THE DRAWINGS

FIG. 1A illustrates a top view of a human finger and a human nail. In FIG. 1A, sign 1 represents the human finger, and sign 2 represents the human nail.

FIG. 1B illustrates a side view of a human finger and a human nail. In FIG. 1B, sign 1 represents the human finger, and sign 2 represents the human nail.

FIG. 2 illustrates a top view of a form. The form is a film for masking portions of a finger other than a nail along a line of the nail. In FIG. 2, sign 3 represents the form.

FIG. 3A illustrates a top view of a state in which a form is inserted into a gap in a human nail and is fixed. In FIG. 3A, sign 2 represents the human nail, and sign 3 represents the form.

FIG. 3B illustrates a side view of a state in which a form is inserted into a gap in a human nail and is fixed. In FIG. 3B, sign 2 represents the human nail, and sign 3 represents the form.

FIG. 4 illustrates a side view of a state in which a photocurable composition is applied on a nail and a form while the form is fixed, the photocurable composition is cured by light irradiation, and the cured product is extended by repeating application and light irradiation. In FIG. 4, sign 3 represents the form, and sign 4 represents the cured product of the photocurable composition.

FIG. 5 illustrates a side view of a state in which a form is removed after a sculptured nail having a predetermined length is formed. In FIG. 5, sign 5 represents the sculptured nail.

FIG. 6 illustrates a result of differential scanning calorimetry (DSC) obtained by irradiating photocurable compositions in Examples 1 to 4 and Comparative Examples 1 to 3 with an active energy ray. Here, the horizontal axis indicates time (minute), and the vertical axis indicates DSC (µW). In FIG. 6, sign 6 represents a result of DSC measurement in Example 1, sign 7 represents a result of DSC measurement in Example 2, sign 8 represents a result of DSC measurement in Example 3, sign 9 represents a result of DSC measurement in Example 4, sign 10 represents a result of DSC measurement in Comparative Example 1, sign 11 represents a result of DSC measurement in Comparative Example 2, and sign 12 represents a result of DSC measurement in Comparative Example 3.

DETAILED DESCRIPTION

A photocurable composition for coating a nail or an artificial nail (hereinafter, also referred to as "photocurable composition" or simply as "composition") according to the present invention contains an acrylate oligomer as a component (A), a methacrylate monomer as a component (B), and a photopolymerization initiator as a component (C).

The composition can be cured with a small amount of heat generation by light irradiation. Therefore, even when a relatively large amount of composition is applied and cured, the amount of heat generation is small. Accordingly, the composition is suitable for extending or reinforcing a nail (natural nail), and is used suitably for a sculptured nail. When the composition is applied on a nail chip (artificial nail) formed of a resin or the like, and decoration is performed, a damage of the nail chip can be suppressed due to the small amount of heat generation, and the nail chip having an excellent appearance can be produced.

Furthermore, the composition has a relatively low viscosity, and therefore has excellent workability. In addition, a deep portion of the composition can be cured by irradiation with an active energy ray such as light (that is, the composition has high curability in a deep portion).

In addition, a cured product formed by irradiating the composition with light (with an active energy ray) has excellent gloss, an excellent appearance, and high hardness, and is not broken easily. Therefore, the cured product formed by curing the composition has also excellent durability.

Hereinafter, the composition according to the present invention will be described in detail. "X to Y" is used here as a meaning including values described at ends thereof (X and Y) as a lower limit value and an upper limit value. Unless otherwise specified, operations and measurement of physical properties or the like are performed under the conditions of room temperature (20 to 25° C.)/relative humidity of 40 to 50% RH.

<Photocurable Composition for Coating Nail or Artificial Nail>

[Component (A)]

The component (A) contained in the composition according to the present invention is an acrylate oligomer (acryloyl group-containing oligomer). The acrylate oligomer is an oligomer having one or more acryloyl groups (acrylic group; $H_2C=CH-C(=O)-$). Here, the "oligomer" means a substance having a weight average molecular weight of more than 1,000. The weight average molecular weight of the component (A) is preferably more than 1,000 and 10,000 or less, more preferably from 2,000 to 6,000, and particularly preferably from 3,000 to 5,000. Within this range, hardness of a cured product can be increased. Here, as the weight average molecular weight, a value measured by gel permeation chromatography (GPC) using polystyrene as a standard substance is employed.

The component (A) is preferably a liquid (that is, preferably has fluidity) at 25° C. Specifically, the viscosity thereof measured using an EHD type rotatory viscometer at 25° C. is preferably 1,000 mPa·s or more, and more preferably 5,000 mPa·s or more (upper limit: 100,000 mPa·s). Within this range, curability can be improved, and hardness of a cured product obtained can be increased. It is preferable to use the component (A) having excellent compatibility with the component (B) and the component (C) in the present invention.

The number of repeating constituent units in an oligomer as the component (A) is not particularly limited, but is preferably from 2 to 1,000, more preferably from 5 to 800, still more preferably from 10 to 500, and particularly preferably from 20 to 300.

The component (A) contained in the composition according to the present invention only needs to have one or more acryloyl groups in one molecule thereof, and may further contain another functional group. For example, the component (A) may be a compound having one or more epoxy groups and one or more acryloyl groups in one molecule thereof.

Above all, the component (A) preferably has 2 to 10 acryloyl groups in one molecule thereof, and more preferably has two acryloyl groups in one molecule thereof (bifunctional acrylate oligomer) from a viewpoint of improving a curing speed or hardness of a cured product obtained.

Specific examples of the acrylate oligomer are not particularly limited, and include an acrylate oligomer having an ester bond in a molecule thereof, an acrylate oligomer having an ether bond, an acrylate oligomer having a urethane bond, and an epoxy-modified acrylate oligomer. Examples of main skeletons of these oligomers include bisphenol A, novolak phenol, polybutadiene, polyester, polyether, and urethane. However, the main skeletons are not limited thereto. The acrylate oligomer as the component (A) may be a commercial product or a synthetic product.

An acrylate oligomer having an ester bond can be synthesized by forming an ester bond by a reaction between a polyol and a polyvalent carboxylic acid and then adding acrylic acid to an unreacted hydroxyl group. However, a method for synthesizing the acrylate oligomer is not limited to this synthesis method. Specific examples of a commercial product thereof include Aronix (registered trademark) M-6100, M-6200, M-6250, M-6500, M-7100, M-7300K, M-8030, M-8060, M-8100, M-8530, M-8560, and M-9050 manufactured by Toagosei Co., Ltd., and UV-3500BA, UV-3520TL, UV-3200B, and UV-3000B manufactured by The Nippon Synthetic Chemical Industry Co., Ltd. However, the commercial product is not limited thereto.

The acrylate oligomer having an ether bond can be synthesized by adding acrylic acid to a hydroxyl group in a polyether polyol or an aromatic hydroxyl group such as bisphenol. However, a method for synthesizing the acrylate oligomer is not limited to this synthesis method. Specific examples of a commercial product thereof include UV-6640B, UV-6100B, and UV-3700B manufactured by The Nippon Synthetic Chemical Industry Co., Ltd, 3EG-A, 4EG-A, 9EG-A, 14EG-A, PTMGA-250, BP-4EA, BP-4PA, and BP-10EA in light (meth)acrylate series manufactured by Kyoeisha Chemical Co., Ltd., and EBECRYL3700 manufactured by Daicel Cytec Co., Ltd. However, the commercial product is not limited thereto.

The acrylate oligomer having a urethane bond can be synthesized by forming a urethane bond by a reaction between a polyol and a polyisocyanate and then adding acrylic acid to an unreacted hydroxyl group. However, a method for synthesizing the acrylate oligomer is not limited to this synthesis method. Specific examples of a commercial product thereof include AH-600, AT-600, UA-306H, and UF-8001G manufactured by Kyoeisha Chemical Co., Ltd. However, the commercial product is not limited thereto.

The acrylate oligomer as the component (A) may be used singly or in combination of two or more kinds thereof.

In the composition according to the present invention, the component (A) preferably contains an acrylate oligomer having a urethane bond (urethane-modified acrylate oligomer; acrylate oligomer having a urethane bond as a main skeleton) from a viewpoint of improving curability of the composition.

[Component (B)]

The component (B) contained in the composition according to the present invention is a methacrylate monomer (methacryloyl group-containing monomer). The methacrylate monomer is a monomer having one or more methacryloyl groups (methacrylic group; $H_2C=C(CH_3)-C(=O)-$) in a molecule thereof. When the composition contains no component (B), the amount of heat generation during curing is large (refer to Comparative Examples 1 to 3). It is considered that this is because a polymerization speed of a methacrylate monomer is moderately low, curing of the composition proceeds gradually, latent heat during curing is reduced, and the amount of heat generation can be thereby reduced. On the other hand, when an acrylate monomer which is a polymerizable monomer like the methacrylate monomer is used, a polymerization speed of the acrylate monomer is high. It is considered that by curing a large amount of the monomer at once, latent heat in the composition is increased and the amount of heat generation is increased. Therefore, the composition according to the present invention preferably contains substantially no acrylate monomers as a polymerizable monomer. However, the above mechanism is based on presumption, and the present invention is not in any way limited to the mechanism.

In order to reduce viscosity of the composition and to improve workability during application, the molecular weight of the component (B) is preferably 1,000 or less, and more preferably 500 or less. The molecular weight of the component (B) can be measured by a known method such as a gas chromatography mass spectrometry (GC-MS) method. In addition, the molecular weight of the component (B) can be identified by identifying a structure of the component (B) by a method such as NMR and performing calculation based on the structure.

The component (B) is preferably a liquid (that is, the component (B) has preferably fluidity) at 25° C. from a viewpoint of workability such as an application property. Specifically, the viscosity thereof measured using an EHD type rotatory viscometer at 25° C. is preferably 1,000 mPa·s or less, and more preferably 500 mPa·s or less (lower limit: 1 mPa·s).

A methacrylate monomer as the component (B) preferably has one to three methacryloyl groups (that is, the component (B) is preferably a mono- to tri-functional methacrylate monomer). Furthermore, the component (B) preferably contains a trifunctional methacrylate monomer from a viewpoint of improving curability in a deep portion of the composition and obtaining a cured product having high hardness.

Specific examples of the monofunctional methacrylate monomer as the component (B) include a methacrylate having a chain structure, such as methacrylic acid, lauryl methacrylate, stearyl methacrylate, ethyl carbitol methacrylate, methoxy diethylene glycol methacrylate, ethoxy diethylene glycol methacrylate, butoxyethyl methacrylate, butoxy triethylene glycol methacrylate, 2-ethylhexyl polyethylene glycol methacrylate, methoxy dipropylene glycol methacrylate, 2-hydroxyethyl methacrylate, 2-hydroxypropyl methacrylate, glycerol methacrylate, polyethylene glycol methacrylate, polypropylene glycol methacrylate, ethylene oxide-modified succinic acid methacrylate, caprolactone-modified 2-hydroxyethyl methacrylate, N,N-dimethylaminoethyl methacrylate, or N,N-diethylaminoethyl methacrylate; a methacrylate having an alicyclic structure, such as cyclohexyl methacrylate, dicyclopentanyl methacrylate or isobornyl methacrylate; a methacrylate having an aromatic ring structure, such as benzyl methacrylate, phenyl methacrylate, phenoxyethyl methacrylate, phenoxy diethylene glycol methacrylate, phenoxy tetraethylene glycol methacrylate, nonyl phenoxyethyl methacrylate, nonylphenoxy tetraethylene glycol methacrylate, nonylphenyl polypropylene glycol methacrylate, or ethylene oxide-modified phthalic acid methacrylate; a methacrylate having a heterocyclic structure, such as tetrahydrofurfuryl methacrylate, caprolactone-modified tetrahydrofurfuryl methacrylate, glycidyl methacrylate, or morpholinoethyl methacrylate; ethylene oxide-modified phosphoric acid methacrylate; and a methacrylamide compound such as methacrylamide, N-methyl methacrylamide, N-ethyl methacrylamide, N-propyl methacrylamide, N-isopropyl methacrylamide, N-n-butyl methacrylamide, N-tert-butyl methacrylamide, N-butoxymethyl methacrylamide, N-methylol methacrylamide, N,N-dimethyl methacrylamide, 4-methacryloyl morpholine, N,N-diethyl methacrylamide, N-methyl-N-ethyl methacrylamide, or N-hydroxyethyl methacrylamide. However, the monofunctional methacrylate monomer is not limited thereto.

Specific examples of the bifunctional methacrylate monomer as the component (B) include a methacrylate having a chain structure, such as 1,3-butylene glycol dimethacrylate, 1,4-butylene glycol dimethacrylate, neopentyl glycol dimethacrylate, 1,6-hexane glycol dimethacrylate, ethylene glycol dimethacrylate, polyethylene glycol dimethacrylate, propylene glycol dimethacrylate, tripropylene glycol dimethacrylate, ethylene oxide-modified neopentyl glycol dimethacrylate, propylene oxide-modified neopentyl glycol dimethacrylate, hydroxypivalate neopentyl glycol dimethacrylate, caprolactone-modified hydroxypivalate neopentyl glycol dimethacrylate, neopentyl glycol-modified trimethylolpropane dimethacrylate, or stearic acid-modified pentaerythritol dimethacrylate; a methacrylate having an alicyclic structure, such as dimethylol tricyclodecane dimethacrylate, dicyclopentenyl dimethacrylate, or ethylene oxide-modified dicyclopentenyl dimethacrylate; a methacrylate having an aromatic ring structure, such as bisphenol A dimethacrylate, ethylene oxide-modified bisphenol A dimethacrylate, or ethylene oxide-modified bisphenol S dimethacrylate; and a methacrylate having a heterocyclic structure, such as dimethacryloyl isocyanurate. However, the bifunctional methacrylate monomer is not limited thereto.

Specific examples of the trifunctional methacrylate monomer as the component (B) include a methacrylate having a chain structure, such as trimethylolpropane trimethacrylate, pentaerythritol trimethacrylate, ethylene oxide-modified trimethylolpropane trimethacrylate, or propylene oxide-modified trimethylolpropane trimethacrylate; and a methacrylate having a heterocyclic structure, such as tris(methacryloyloxy ethyl) isocyanurate. However, the trifunctional methacrylate monomer is not limited thereto.

The methacrylate monomer as the component (B) may be used singly or in combination of two or more kinds thereof.

In the composition according to the present invention, the component (B) preferably contains a polyfunctional methacrylate monomer having a chain structure and/or a methacrylate monomer having an alicyclic structure from a viewpoint of suppressing generation of heat during curing. The component (B) more preferably contains a trifunctional methacrylate monomer having a chain structure and/or a methacrylate monomer having an alicyclic structure from a similar viewpoint. In addition, the component (B) still more preferably contains trimethylolpropane trimethacrylate and/or a methacrylate monomer having an alicyclic structure from a similar viewpoint. In addition, the component (B) is particularly preferably trimethylolpropane trimethacrylate and/or a methacrylate monomer having an alicyclic structure alone from a viewpoint of maintaining hardness of a cured product favorably.

Here, the "methacrylate monomer having a chain structure" means a methacrylate monomer having no cyclic structures. The "chain structure" includes a linear chain structure and a branched chain structure. The "methacrylate monomer having an alicyclic structure" means a methacrylate monomer having a hydrocarbon cyclic structure. Examples of the alicyclic structure include a monocyclic cycloalkyl group such as a cyclopropyl group, a cyclobutyl group, a cyclopentyl group, a cyclohexyl group, a methyl cyclohexyl group, or a dimethyl cyclohexyl group; a monocyclic cycloalkenyl group such as a cyclobutenyl group, a cyclopentenyl group, or a cyclohexenyl group; a polycyclic cycloalkyl group such as a hydronaphthyl group, a 1-adamantyl group, a 2-adamantyl group, a norbornyl group, a methyl norbornyl group, an isobornyl group, a dicyclopentanyl group, a tricyclodecyl group, or a tetracyclododecyl group; and a polycyclic cycloalkenyl group such as a dicyclopentenyl group or a dicyclopentenyl oxyethyl group. However, the alicyclic structure is not limited thereto.

One kind or two or more kinds of the alicyclic structure may be included in one molecule. Among the above alicyclic structures, the component (B) preferably has a polycyclic cycloalkyl group as the alicyclic structure from a viewpoint of obtaining an effect of the present invention easily.

Examples of a methacrylate monomer having such a polycyclic cycloalkyl group include the above compounds. Above all, the composition according to the present invention preferably contains isobornyl methacrylate or dimethylol tricyclodecane dimethacrylate as the component (B) from a viewpoint of suppressing generation of heat during curing.

As described above, the composition according to the present invention may contain a monofunctional monomer having a hydroxyl group as the component (B). Specific examples thereof include 2-hydroxyethyl methacrylate and 2-hydroxypropyl methacrylate. However, the monofunctional monomer is not limited thereto.

The component (B) may be a commercial product or a synthetic product. Specific examples of a commercial product thereof include a polyfunctional methacrylate TMPT, bifunctional methacrylates 2G and 4G, and a monofunctional methacrylate S manufactured by Shin-Nakamura Chemical Co., Ltd.; and a light ester (registered trademark, the same applies to the following) PO, IB-X, and DPC-M manufactured by Kyoeisha Chemical Co., Ltd. However, the commercial product is not limited thereto.

The content (the total content when two or more kinds of components are contained) of the component (B) in the composition of the present invention is preferably from 1 to 50 parts by mass, more preferably from 10 to 50 parts by mass, still more preferably from 20 to 40 parts by mass, and particularly preferably from 25 to 35 parts by mass relative to 100 parts by mass of the component (A). When the content of the component (B) is one part by mass or more, curability in a deep portion and hardness of a cured product can be maintained favorably. On the other hand, when the content of the component (B) is 50 parts by mass or less, generation of heat can be further suppressed during curing.

[Component (C)]

The component (C) contained in the composition according to the present invention is a photopolymerization initiator. The photopolymerization initiator is not limited as long as being a radical-based photopolymerization initiator for generating a radical species by irradiation with an active energy ray such as a visible light, an ultraviolet ray, an X-ray, or an electron beam.

Specific examples of the component (C) include acetophenones such as diethoxyacetophenone, 2-hydroxy-2-methyl-1-phenylpropan-1-one, benzyl dimethyl ketal, 4-(2-hydroxyethoxy) phenyl-(2-hydroxy-2-propyl) ketone, 1-hydroxycyclohexyl phenyl ketone, 2-methyl-2-morpholino (4-thiomethylphenyl) propan-1-one, 2-benzyl-2-dimethylamino-1-(4-morpholinophenyl) butanone, and 2-hydroxy-2-methyl-1-[4-(1-methylvinyl) phenyl]propanone oligomer; benzoins such as benzoin, benzoin methyl ether, benzoin ethyl ether, benzoin isopropyl ether, and benzoin isobutyl ether; benzophenones such as benzophenone, o-benzoyl methyl benzoate, 4-phenyl benzophenone, 4-benzoyl-4'-methyl-diphenyl sulfide, 3,3',4,4'-tetra(t-butyl peroxy carbonyl) benzophenone, 2,4,6-trimethyl benzophenone, 4-benzoyl-N,N-dimethyl-N-[2-(1-oxo-2-propenyloxy) ethyl]benzene methanamium bromide, and (4-benzoylbenzyl) trimethylammonium chloride; thioxanthones such as 2-isopropylthioxanthone, 4-isopropylthioxanthone, 2,4-diethyl thioxanthone, 2,4-dichloro thioxanthone, 1-chloro-4-propoxy thioxanthone, and 2-(3-dimethylamino-2-hydroxy)-3,4-dimethyl-9H-thioxanthon-9-one methocloride; and phosphine oxides such as 2,4,6-trimethyl benzoyl-diphenyl-phosphine oxide and bis(2,4,6-trimethyl benzoyl)-phenyl phosphine oxide. However, the component (C) is not limited thereto. These compounds may be used singly or in combination of two or more kinds thereof.

The content (the total content when two or more kinds of components are contained) of the component (C) in the composition of the present invention is preferably from 0.1 to 20 parts by mass, more preferably from 1 to 15 parts by mass, and particularly preferably from 2 to 10 parts by mass relative to 100 parts by mass of the component (A). When the content of the component (C) is 0.1 parts by mass or more, photocurability can be maintained. On the other hand, when the content of the component (C) is 20 parts by mass or less, storage stability can be maintained without causing thickening during storage.

The component (C) preferably contains a visible light type photopolymerization initiator. Here, the "visible light type photopolymerization initiator" means a photopolymerization initiator having maximum absorption in a visible light region (region in which a wavelength is from 400 to 800 nm, and preferably from 400 to 500 nm), and mainly means a photopolymerization initiator containing a phosphorous atom. Examples of such a photopolymerization initiator include an acylphosphine oxide-based photopolymerization initiator. Specifically, the above compounds exemplified as phosphine oxides can be used. However, the photopolymerization initiator is not limited thereto.

The content of the visible light type photopolymerization initiator contained in the composition according to the present invention is preferably from 0 to 50% by mass, more preferably from 10 to 40% by mass, and particularly preferably from 20 to 30% by mass relative to the total mass of the component (C). Within such a range, a cured product does not cause yellowing easily, and the composition has excellent surface curability.

[Plasticizer]

The composition according to the present invention may contain a plasticizer within such a range not to impair a characteristic of the present invention. Specific examples of the plasticizer include a polycarboxylate-based plasticizer such as an aromatic polycarboxylate; a phthalate-based plasticizer such as dioctyl phthalate (DOP), dibutylphthalate (DBP), diheptyl phthalate (DHP), diisononyl phthalate (DINP), diisodecyl phthalate (DIDP), or butyl benzylphthalate (BBP); a trimellitate-based plasticizer such as trioctyl trimellitate (TOTM) or triisodecyl trimellitate (TITM); a pyromellitate-based plasticizer such as tetra octyl pyromellitate; an aliphatic polycarboxylate-based plasticizer such as di-2-ethylhexyl adipate (DOA), isodecyl adipate (DIDA), di-2-ethylhexyl sebacate (DOS), dibutyl sebacate (DBS), di-2-ethylhexyl maleate (DOM), dibutyl fumarate (DBF), di-2-ethylhexyl azelate (DOZ), di-2-ethylhexyl epoxy hexahydro phthalate, trioctyl citrate, or glycerol triacetate; and a phosphate-based plasticizer such as trimethyl phosphate, tributyl phosphate, tri(2-ethylhexyl) phosphate, tributoxyethyl phosphate, triphenyl phosphate, tricresyl phosphate, an alkyl aryl phosphate, triethyl phosphate, tri(chloroethyl) phosphate, trisdichloropropyl phosphate, tris(β-chloropropyl) phosphate, octyl diphenyl phosphate, tris(isopropylphenyl) phosphate, or cresyl phenyl phosphate. However, the plasticizer is not limited thereto. These compounds may be used singly or in combination of two or more kinds thereof.

Above all, the composition preferably contains an aliphatic polycarboxylate as a plasticizer from a viewpoint of making a cured product obtained by curing the composition glossy and making an appearance thereof excellent.

The content (the total content when two or more kinds of components are contained) of a plasticizer in the composition of the present invention is preferably from 0.1 to 10 parts by mass, and more preferably from 3 to 5 parts by mass relative to 100 parts by mass of the component (A). When the content of the plasticizer is 0.1 parts by mass or more, a scratch is hardly generated and gloss is exhibited at the time of wiping a surface of a cured product with a waste impregnated with ethanol. On the other hand, when the content of the plasticizer is 10 parts by mass or less, a scratch is hardly generated on the cured product over time, and gloss can be maintained.

[Other Components]

The composition according to the present invention may contain components other than the above components (A) to (C) within such a range not to impair a characteristic of the present invention. Examples of such a component include a colorant such as a pigment or a dye; an inorganic filler such as metal powder, calcium carbonate, talc, silica, amorphous silica, alumina, or aluminum hydroxide; an organic filler such as a polystyrene filler, a poly(meth)acrylic filler, or a rubber filler; a flame retardant; an antioxidant; a polymerization inhibitor; a defoamer; a coupling agent; a leveling agent; and a rheology control agent. By addition of these other components, a composition having excellent resin strength, bonding strength, workability, storage performance, or the like, and a cured product thereof can be obtained. The content of these components in the composition is preferably 0.1% by mass or less (lower limit: 0% by mass) from a viewpoint of maintaining transparency of a cured product formed or hardness thereof favorably.

On the other hand, the composition according to the present invention preferably contains substantially no solvents from a viewpoint of suppressing curing contraction during curing. By containing substantially no solvent, change in size of a cured product caused by a solvent can be suppressed. Here, the "solvent" means a solvent which can dissolve the components (A) to (C) contained in the composition. Examples thereof include a ketone-based solvent, an alcohol-based solvent, a glycol-based solvent, a hydrocarbon-based solvent, and an ester-based solvent.

Here, "not substantially contain" means that the composition may contain an object substance by contamination while the content of the object substance is 0.1% by mass or less (lower limit: 0% by mass) relative to the total amount of the composition.

[Composition Ratio]

In the composition according to the present invention, the contents of the above components are preferably within the following ranges from a viewpoint of suppressing the amount of heat generation during curing. That is, the content of the component (A) is preferably from 50 to 80% by mass, and more preferably from 55 to 75% by mass relative to the total amount of the composition. The content of the component (B) is preferably from 10 to 40% by mass, and more preferably from 15 to 35% by mass relative to the total amount of the composition. The content of the component (C) is preferably from 1 to 10% by mass, and more preferably from 5 to 8% by mass relative to the total amount of the composition.

When the composition contains a plasticizer, the content of the plasticizer is preferably from 0.1 to 8% by mass, and more preferably from 1 to 5% by mass relative to the total amount of the composition.

Here, the composition according to the present invention preferably contains substantially no methacrylate oligomers or acrylate monomers. Not containing such polymerizable components described above in the composition allows generation of heat during curing to be further suppressed advantageously. Definition of "not substantially contain" has been described above.

The composition according to the present invention preferably contains 50 to 80% by mass of the component (A), 10 to 40% by mass of the component (B), 1 to 10% by mass of the component (C), and 0.1 to 8% by mass of a plasticizer, and more preferably contains 55 to 75% by mass of the component (A), 15 to 35% by mass of the component (B), 5 to 8% by mass of the component (C), and 1 to 5% by mass of a plasticizer from a viewpoint of decreasing the amount of heat generation during curing and improving curability (the total content of the components (A) to (C) and the plasticizer above is 100% by mass).

[Viscosity]

When a nail is coated (decorated) using the composition according to the present invention, it is preferable to apply the composition on a nail or a form and then to cure the composition by irradiation with an active energy ray (UV light or the like). Therefore, the composition is preferably applied easily from a viewpoint of workability. Specifically, the viscosity at 25° C. of the composition according to the present invention is preferably from 20 to 200 Pa·s, and more preferably from 30 to 150 Pa·s from a viewpoint of workability such as easiness of application. Within such a range, the composition is applied easily because of moderate fluidity, and forming of a decorated portion is performed easily. Specifically, a value measured by a method described in Examples is employed as the viscosity of the composition. The viscosity of the composition can be adjusted by selecting the above components (A) to (C) appropriately.

<Use Application>

The composition according to the present invention is mainly used for coating (decorating) a nail or an artificial nail such as a nail chip by curing the composition after the composition is applied on the nail or the artificial nail. The composition according to the present invention has a small amount of heat generation when being cured by irradiation with an active energy ray (light or the like), and therefore can be applied directly on a nail (natural nail), and is suitable for thick application. Therefore, the composition according to the present invention is suitable for extending a nail or increasing the thickness of the nail, and therefore can be used suitably for extension of the nail or reinforcement thereof. That is, a preferable embodiment of the present invention is the photocurable composition for coating a nail or an artificial nail, used for a sculptured nail formed for extension of a nail or reinforcement thereof.

In addition, a preferable embodiment of the present invention is an artificial nail obtained (obtainable) by curing the photocurable composition for coating a nail or an artificial nail. Such an artificial nail can be produced by applying the composition according to the present invention on a nail chip formed in advance and then curing the composition by irradiation with an active energy ray (light or the like). In addition, the artificial nail can be produced by molding the composition appropriately and then curing the composition by irradiation with an energy ray (light or the like).

<Method for Coating (Decorating) Nail>

A method for coating (decorating) a nail using the composition according to the present invention is not particularly limited as long as being able to mold the composition into a proper shape and to cure the composition. However, the following method is preferable.

That is, a preferable embodiment of the present invention is a method for coating a nail, including repeating a process for applying a photocurable composition for coating a nail or an artificial nail containing the following components (A) to (C) on a nail (natural nail) and then curing the photocurable composition for coating a nail or an artificial nail by irradiation with an active energy ray.

a component (A): an acrylate oligomer;
a component (B): a methacrylate monomer; and
a component (C): a photopolymerization initiator.

A method for applying the composition or a method for curing the composition is not particularly limited, but a method known to a person skilled in the art can be used.

Before a nail is coated with the composition according to the present invention, it is preferable to sand a surface of a human nail (natural nail) using a file or the like and then to remove dust, oil, water, or the like using a solvent used exclusively for a nail containing ethanol mainly.

A method for applying the composition according to the present invention on a nail (natural nail) is not particularly limited. However, the composition is preferably applied using a writing brush, a brush, or the like. In this case, the thickness of the composition applied is preferably from 100 to 2,000 μm, and more preferably from 500 to 1,500 μm before curing. A primer may be used (applied) before the composition is applied.

As a method for curing the composition according to the present invention, the composition is preferably cured by irradiation with an active energy ray. An active energy ray irradiation apparatus for curing is not particularly limited, and a commercially available UV lamp or LED lamp can be used. Irradiation time is not particularly limited, but is preferably from 10 seconds to 120 seconds, and more preferably from 10 seconds to 70 seconds considering an effect on a finger. The accumulated amount of light is preferably from 5 to 60 kJ/m².

Specifically, a nail can be coated (decorated) according to the following procedures. First, a form illustrated in FIG. 2 is inserted into a gap in a nail (natural nail) as illustrated in FIG. 3, and is fixed to a finger, and the composition according to the present invention is applied on the nail (natural nail) and the form as illustrated in FIG. 4. Thereafter, the composition is cured by irradiation with an active energy ray as illustrated in FIG. 5, and the nail is thereby coated (decorated). The length of the nail (decorated portion) can be increased by repeating a process for applying the composition and curing the composition by irradiation with an active energy ray. The thickness of the nail (decorated portion) can be increased by further applying the composition again on a surface of a cured product obtained by curing the composition. By repeating a process for applying and curing the composition in this way, the cured product is formed and the nail is extended or reinforced, and then the cured product may be cut into an appropriate shape for shaping. A method for shaping is not particularly limited, but a known method can be used.

EXAMPLES

Next, the present invention will be described in more detail based on Examples, but the present invention is not limited only to these Examples. In the following Examples, unless otherwise specified, an operation was performed at room temperature (25° C.). Unless otherwise specified, "%" and "part" mean "% by mass" and "part by mass", respectively.

Examples 1 to 4 and Comparative Examples 1 to 3

The following components were prepared in order to prepare a photocurable composition for coating a nail or an artificial nail.

[Component (A): Acrylate Oligomer]
  non-yellowing type oligourethane acrylate (bifunctional) (UF-8001G manufactured by Kyoeisha Chemical Co., Ltd.; weight average molecular weight 4,500)

[Component (B): Methacrylate Monomer]
  trimethylolpropane trimethacrylate (TMPT manufactured by Shin-Nakamura Chemical Co., Ltd.)
  isobornyl methacrylate (light ester IB-X manufactured by Kyoeisha Chemical Co., Ltd.; referred to as "IB-X" in the following Table 1)
  dimethylol tricyclodecane dimethacrylate (light ester DCP-M manufactured by Kyoeisha Chemical Co., Ltd.; referred to as "DCP-M" in the following Table 1)

[Component (B'): Monomer Other than Component (B)]
  trimethylolpropane triacrylate (A-TMPT manufactured by Shin-Nakamura Chemical Co., Ltd.)
  isobornyl acrylate (light acrylate (registered trademark) IB-XA manufactured by Kyoeisha Chemical Co., Ltd.; referred to as "IB-XA" in the following Table 1)
  dimethylol tricyclodecane diacrylate (DCP-A manufactured by Kyoeisha Chemical Co., Ltd.; referred to as "DCP-A" in the following Table 1)

[Component (C): Photopolymerization Initiator]
  1-hydroxycyclohexyl phenyl ketone (non-visible light type photopolymerization initiator) (Suncure (registered trademark) 84 manufactured by Chemark Chemical Co., Ltd.; referred to as "84" in the following Table 1)
  2,4,6-trimethyl benzoyl-diphenyl-phosphine oxide (visible light type photopolymerization initiator) (LUCIRIN (registered trademark) TPO manufactured by BASF SE; referred to as "TPO" in the following Table 1)

[Plasticizer]
  di-2-ethylhexyl sebacate (sansocizer DOS manufactured by New Japan Chemical Co., Ltd.; referred to as "DOS" in the following Table 1)

The above components were blended in the amounts (parts by mass) described in the following Table 1 to prepare a composition. Specifically, the component (A), the component (B) (or component (B')), and a plasticizer were weighed and put into a stirring pot, and then were stirred for thirty minutes while being subjected to vacuum defoaming. Thereafter, the component (C) was weighed and put into the stirring pot, and the resulting mixture was stirred further thirty minutes while being subjected to vacuum defoaming.

TABLE 1

| component | raw material | Example 1 | Example 2 | Example 3 | Example 4 | Comparative Example 1 | Comparative Example 2 | Comparative Example 3 |
|---|---|---|---|---|---|---|---|---|
| Component (A) | UF-8001G | 100 | 100 | 100 | 100 | 100 | 100 | 100 |
| Component (B) | TMPT | 15 | 35 | | | | | |
| | IB-X | 20 | | 35 | | | | |
| | DCP-M | | | | 35 | | | |
| Component (B') | A-TMPT | | | | | 35 | | |
| | IB-XA | | | | | | 35 | |
| | DCP-A | | | | | | | 35 |
| Component (C) | 84 | 7 | 7 | 7 | 7 | 7 | 7 | 7 |
| | TPO | 2 | 2 | 2 | 2 | 2 | 2 | 2 |
| plasticizer | DOS | 4 | 4 | 4 | 4 | 4 | 4 | 4 |
| | total | 148 | 148 | 148 | 148 | 148 | 148 | 148 |

Measurement of viscosity, confirmation of gloss, confirmation of curability in a deep portion, measurement of hardness, DSC measurement, and confirmation of heat generation by a sensory test were performed for compositions obtained in Examples 1 to 4 and Comparative Examples 1 to 3. Table 2 indicates results thereof. Details of evaluations are as follows.

[Measurement of Viscosity]

0.5 mL of each of the compositions in Examples 1 to 4 and Comparative Examples 1 to 3 was collected and discharged into a measuring cup. Viscosity was measured under the following conditions using an EHD type viscometer (manufactured by Toki Sangyo Co., Ltd.). A result thereof was shown as "viscosity (Pa s)". The viscosity of a composition is preferably from 20 to 200 Pas when a nail is coated (decorated) with the composition from a viewpoint of workability such as suppression of flowing of the composition or easiness of application.

<<Measurement Conditions>> cone rotor: 3°×R14
rotational speed: 1 rpm
measurement time: 3 minutes
measurement temperature: 25° C. (temperature was controlled using a thermostatic tank)

[Confirmation of Gloss]

On a test piece obtained by subjecting a steel plate cold commercial-SD (SPCC-SD, dull-finished) to a black chemical conversion treatment and then to electrodeposition coating (refer to JIS G 3141:2011 for details), each of the compositions in Examples 1 to 4 and Comparative Examples 1 to 3 was applied so as to have a dry thickness of 100 µm. Thereafter, each of the compositions was cured by irradiation with a LED lamp for a nail (rated voltage: 240 V, 50 to 60 Hz, power consumption: 30 W, wavelength: 400 to 410 nm) for 10 seconds. A surface of the cured product was wiped off with a waste impregnated with ethanol three times. Ethanol was dried, and then a result confirmed visually based on the following evaluation standard was shown as "gloss". When the obtained product is used for a sculptured nail, the product is preferably evaluated as "O" from a viewpoint of appearance.

<<Evaluation Standard>>

O: glossy
x: not glossy

[Confirmation of Curability in Deep Portion]

Three washers each having an inner diameter of 6.5φ and a thickness of 1 mm were stacked on a polytetrafluoroethylene plate, and each of the compositions in Examples 1 to 4 and Comparative Examples 1 to 3 was poured into a hole of the washers. Each of the compositions was cured by irradiation with a UV lamp for a nail (rated voltage: AC 100 V, 50 to 60 Hz, power consumption: 36 W, wavelength: 350 to 400 nm) for 60 seconds. Separately, each of the compositions was cured by irradiation with a LED lamp for a nail (rated voltage: 240 V, 50 to 60 Hz, power consumption: 30 W, wavelength: 400 to 410 nm) for 10 seconds. After irradiation, the cured product was removed from the washers, an uncured portion of each of the compositions was wiped off, and then the thickness of the cured product was measured using calipers. The thickness of the cured product due to the UV lamp for a nail was shown as "curability in a deep portion 1 (mm)". The thickness of the cured product due to the LED lamp for a nail was shown as "curability in a deep portion 2 (mm)". Curability in a deep portion 1 is preferably 0.5 mm or more, and curability in a deep portion 2 is preferably 1.0 mm or more from a viewpoint of workability.

[Measurement of Hardness]

Light irradiation was performed twice using a conveyor type irradiation apparatus having a high pressure mercury lamp mounted thereon with the thickness of each of the compositions in Examples 1 to 4 and Comparative Examples 1 to 3 being 1 mm (each accumulated amount of light 30 kJ/m$^2$), and a sheet-shaped cured product was produced. When the temperature of the cured product became 25° C., the cured products were laminated to form three layers. While a pressurizing surface of a D type durometer (hardness meter) was maintained so as to be parallel to the sheet-shaped cured product, the pressurizing surface was pressed with a 10 N force rapidly without an impact, and the pressurizing surface was brought into close contact with a sample. A maximum value was read during measurement, and was shown as "hardness (no unit)". Details thereof are in accordance with JIS K 6253-3:2012. It can be said that the cured product having D50 or more secures hardness which can be used for top coating.

[DSC Measurement]

Differential scanning calorimetry (DSC) was performed during irradiation with an active energy ray. 0.8 mg of each of the compositions in Examples 1 to 4 and Comparative Examples 1 to 3 was weighed and put into an aluminum sample pan. The sample pan was set at a predetermined position in a measurement apparatus, and a vacant sample pan was set at a predetermined position for reference. A quartz cell was set between the sample pan and a high pressure mercury lamp. Measurement was started in a measurement environment of 25° C. A sample was allowed to stand at 25° C. for one minute, was then irradiated with the high pressure mercury lamp at 3 mW for two minutes, and was finally allowed to stand at 25° C. for one minute.

Measurement was performed for four minutes in total. FIG. 6 illustrates measurement results thereof. In FIG. 6, the horizontal axis indicates time (minute), and the vertical axis indicates DSC (μW) (differential scanning calorie: change in heat flow in accordance with heat absorption and heat generation). FIG. 6 illustrates an enlarged portion of 1.0 to 1.2 minutes in the X axis. A maximum value of DDSC (μW/minute) (differential value of DSC and an inclination of a tangent of DSC) calculated at the same time as measurement was confirmed, and the maximum value of DDSC was shown as "DSC heat generation (μW/minute)". Initial heat generation is preferably 1,000,000 μW/minute or less such that a human does not feel hot at a nail.

[Confirmation of Heat Generation by Sensory Test]

Each of the compositions in Examples 1 to 4 and Comparative Examples 1 to 3 was applied on a nail of a human hand so as to have a dry thickness of 100 μm, and was then irradiated with the LED lamp for a nail for 10 seconds to cure each of the compositions. During curing, "heat generation" was confirmed based on the following evaluation standard. The obtained product is preferably evaluated as "○" such that a human does not feel hot at a nail.

<<Evaluation Standard>>

○: A human does not feel hot at a nail.

x: A human feels hot at a nail.

TABLE 2

| test item | Example 1 | Example 2 | Example 3 | Example 4 | Comparative Example 1 | Comparative Example 2 | Comparative Example 3 |
|---|---|---|---|---|---|---|---|
| viscosity (Pa·s) | 65 | 71 | 50 | 122 | 80 | 42 | 121 |
| gloss | ○ | ○ | ○ | ○ | ○ | ○ | ○ |
| curability in a deep portion 1 (mm) | 0.9 | 0.7 | 0.8 | 0.8 | 0.7 | 0.8 | 0.8 |
| curability in a deep portion 2 (mm) | 1.1 | 1.2 | 1.1 | 1.0 | 1.3 | 1.3 | 1.3 |
| hardness | D75 | D70 | D68 | D69 | D70 | D60 | D70 |
| DSC heat generation (μW/minute) | 640,560 | 325,932 | 534,009 | 343,070 | 1,211,695 | 1,101,470 | 1,097,382 |
| heat generation | ○ | ○ | ○ | ○ | x | x | x |

Comparison among Examples 1 to 4 and Comparative Examples 1 to 3 indicates that there is no large difference in the item of "viscosity", "gloss", "curability in a deep portion 1", "curability in a deep portion 2", or "hardness". However, it is found that there is a large difference in the items of "DSC heat generation" and "heat generation". "DSC heat generation" which is a maximum value of DDSC as an inclination of a tangent of DSC indicates that an inclination is sharply increased immediately after curing is started by light irradiation and that heat generation per unit time is large in Comparative Examples 1 to 3. In accordance therewith, there is a large difference in the amount of heat generation felt by a human body in the item of "heat generation". Specifically, the compositions of Examples 1 to 4 gave no hot feel but the compositions of Comparative Examples 1 to 3 gave a hot feel. This indicates that use of a methacrylate as the component (B) allows heat generation to be suppressed.

Even when a large amount of the composition according to the present invention is applied, the amount of heat generation during curing is small. Therefore, the composition according to the present invention can be applied thickly. In addition, the composition according to the present invention does not require cooling when being applied again, and therefore can reduce time for operation. In addition, the composition according to the present invention has high curability in a deep portion, and can form a cured product having high hardness. In addition, the composition according to the present invention exhibits excellent gloss, and therefore has an excellent appearance. Therefore, the photocurable composition for coating a nail or an artificial nail according to the present invention can be used suitably as a UV nail gel suitable for a sculptured nail.

Application of the present invention is not limited to the above embodiments, but can be modified appropriately within such a range not to depart from a gist of the present invention.

What is claimed is:

1. A photocurable composition for coating a nail or an artificial nail, comprising:
    a component (A): an acrylate oligomer comprising a bifunctional urethane-modified acrylate oligomer;
    a component (B): a methacrylate monomer comprising a monomer selected from the group consisting of a trimethylolpropane trimethacrylate, isobornyl methacrylate, dimethylol tricyclodecane dimethacrylate, and mixtures thereof, where component (B) is included in an amount of 1 to 50 parts by mass relative to 100 parts by mass of component (A); and
    a component (C): a photopolymerization initiator;
    and where said photocurable composition for coating a nail or an artificial nail has a viscosity at 25° C. of 30 to 200 Pa·s.

2. The photocurable composition for coating a nail or an artificial nail according to claim 1, comprising substantially no methacrylate oligomers or acrylate monomers.

3. The photocurable composition for coating a nail or an artificial nail according to claim 1, wherein the component (B) is trimethylolpropane trimethacrylate.

4. The photocurable composition for coating a nail or an artificial nail according to claim 1, which has a viscosity at 25° C. of 30 to 150 Pa·s.

5. The photocurable composition for coating a nail or an artificial nail according to claim 1, comprising substantially no solvents.

6. An artificial nail obtained by curing the photocurable composition for coating a nail or an artificial nail according to claim 1.

7. The photocurable composition for coating a nail or an artificial nail according to claim 1, wherein the component (B) has a molecular weight of 1,000 or less.

8. The photocurable composition for coating a nail or an artificial nail according to claim 1, wherein the component (A) has a weight average molecular weight of more than 1,000.

9. The photocurable composition for coating a nail or an artificial nail according to claim 1, wherein the component (A) has a weight average molecular weight of more than 1,000 and the component (B) has a molecular weight of 1,000 or less.

10. A method for coating a nail, comprising repeating a process for applying the photocurable composition for coating a nail or artificial nail according to claim 1 on a nail and then curing the photocurable composition for coating a nail or an artificial nail by irradiation with an active energy ray.

* * * * *